United States Patent
Zylber et al.

(10) Patent No.: US 10,631,898 B2
(45) Date of Patent: Apr. 28, 2020

(54) SPINAL STABILIZATION SYSTEM WITH RIGID AND FLEXIBLE ELEMENTS

(71) Applicant: Zimmer Spine, Inc., Edina, MN (US)

(72) Inventors: Emmanuel Zylber, Marseilles (FR); Thomas Egli, Volketswil (CH); Rosemary E. Thompson, Elgg (CH); Markus Froehlich, Balterswil (CH); Giuseppe Cicerchia, Winterthur (CH); Jack A. Dant, St. Paul, MN (US); Thomas O. Viker, New Brighton, MN (US); Kevin R. Ley, Elk River, MN (US)

(73) Assignee: Zimmer Spine, Inc., Edina, MN (US)

( * ) Notice: Subject to any disclaimer, the term of this patent is extended or adjusted under 35 U.S.C. 154(b) by 79 days.

(21) Appl. No.: 15/861,320

(22) Filed: Jan. 3, 2018

(65) Prior Publication Data
US 2018/0125534 A1    May 10, 2018

Related U.S. Application Data

(60) Division of application No. 14/705,575, filed on May 6, 2015, now Pat. No. 9,888,944, which is a
(Continued)

(51) Int. Cl.
*A61B 17/70*    (2006.01)

(52) U.S. Cl.
CPC ...... *A61B 17/7019* (2013.01); *A61B 17/7004* (2013.01); *A61B 17/7005* (2013.01);
(Continued)

(58) Field of Classification Search
CPC ............ A61B 17/7019; A61B 17/7034; A61B 17/7005; A61B 17/7004; A61B 17/7008; A61B 17/7032
See application file for complete search history.

(56) References Cited

U.S. PATENT DOCUMENTS

| 5,540,688 A | 7/1996 | Navas |
| 5,562,660 A | 10/1996 | Grob |

(Continued)

FOREIGN PATENT DOCUMENTS

| EP | 669109 B1 | 5/1999 |
| EP | 1719468 A1 | 11/2006 |

(Continued)

OTHER PUBLICATIONS

"European Application Serial No. 17199929.5, Response filed Sep. 12, 2018 to Extended European Search Report dated Feb. 2, 2018", 15 pgs.

(Continued)

*Primary Examiner* — Ellen C Hammond
(74) *Attorney, Agent, or Firm* — Schwegman Lundberg & Woessner, P.A.

(57) ABSTRACT

A spinal stabilization system generally comprises first and second anchor members configured to be secured to first and second vertebrae within a patient's body, a flexible element secured to the first anchor member, and a rigid element secured to the second anchor member. An end portion of the rigid element is coupled to an end portion of the flexible so that the system is able to provide both rigid and dynamic stabilization. The coupling is maintained even if the flexible element relaxes after a period of time within the patient's body.

19 Claims, 5 Drawing Sheets

Related U.S. Application Data continuation of application No. 13/241,696, filed on Sep. 23, 2011, now Pat. No. 9,034,018, which is a continuation of application No. 11/688,961, filed on Mar. 21, 2007, now Pat. No. 8,057,516.

(52) U.S. Cl.
CPC ........ *A61B 17/705* (2013.01); *A61B 17/7008* (2013.01); *A61B 17/7022* (2013.01); *A61B 17/7031* (2013.01); *A61B 17/7032* (2013.01); *A61B 17/7034* (2013.01)

(56) References Cited

U.S. PATENT DOCUMENTS

| | | |
|---|---|---|
| 6,290,700 B1 | 9/2001 | Schmotzer |
| 6,471,703 B1 | 10/2002 | Ashman |
| 6,610,079 B1 | 8/2003 | Li et al. |
| 6,986,771 B2 | 1/2006 | Paul et al. |
| 6,989,011 B2 | 1/2006 | Paul et al. |
| 7,326,210 B2 | 2/2008 | Jahng |
| 7,942,905 B2 * | 5/2011 | Lim ................ A61B 17/7007 606/246 |
| 8,057,516 B2 | 11/2011 | Emmanuel et al. |
| 8,518,080 B2 * | 8/2013 | Egli .................. A61B 17/705 606/246 |
| 8,740,945 B2 * | 6/2014 | Hestad .............. A61B 17/7008 606/254 |
| 9,034,018 B2 | 5/2015 | Zylber et al. |
| 9,888,944 B2 | 2/2018 | Zylber et al. |
| 2001/0020186 A1 | 9/2001 | Boyce et al. |
| 2002/0035366 A1 * | 3/2002 | Walder .............. A61B 17/7031 606/254 |
| 2004/0133203 A1 | 7/2004 | Young et al. |
| 2004/0220671 A1 | 11/2004 | Ralph et al. |
| 2005/0065516 A1 | 3/2005 | Jahng |
| 2005/0085815 A1 | 4/2005 | Harms et al. |
| 2005/0124991 A1 | 6/2005 | Jahng |
| 2005/0143737 A1 | 6/2005 | Pafford et al. |
| 2005/0149053 A1 | 7/2005 | Varieur et al. |
| 2005/0149191 A1 | 7/2005 | Cragg et al. |
| 2005/0154390 A1 | 7/2005 | Biedermann et al. |
| 2005/0203513 A1 | 9/2005 | Jahng et al. |
| 2005/0203514 A1 | 9/2005 | Jahng et al. |
| 2006/0058800 A1 | 3/2006 | Ainsworth et al. |
| 2006/0111715 A1 | 5/2006 | Jackson |
| 2006/0129149 A1 | 6/2006 | Ott et al. |
| 2006/0142758 A1 | 6/2006 | Petit |
| 2006/0149380 A1 | 7/2006 | Lotz et al. |
| 2007/0005062 A1 | 1/2007 | Lange et al. |
| 2007/0016200 A1 | 1/2007 | Jackson |
| 2007/0055244 A1 | 3/2007 | Jackson |
| 2007/0129729 A1 | 6/2007 | Petit et al. |
| 2007/0198088 A1 | 8/2007 | Biedermann et al. |
| 2007/0270860 A1 | 11/2007 | Jackson |
| 2007/0293862 A1 | 12/2007 | Jackson |
| 2008/0091213 A1 | 4/2008 | Jackson |
| 2008/0140076 A1 | 6/2008 | Jackson |
| 2008/0147122 A1 | 6/2008 | Jackson |
| 2008/0177317 A1 | 7/2008 | Jackson |
| 2008/0183216 A1 * | 7/2008 | Jackson ............... A61B 17/701 606/278 |
| 2008/0215095 A1 * | 9/2008 | Biedermann ...... A61B 17/7031 606/246 |
| 2012/0016421 A1 | 1/2012 | Zylber et al. |
| 2015/0230827 A1 | 8/2015 | Zylber et al. |

FOREIGN PATENT DOCUMENTS

| | | |
|---|---|---|
| EP | 1523949 B1 | 6/2007 |
| FR | 2715057 B1 | 3/1996 |
| FR | 2775583 A1 | 9/1999 |
| FR | 2844180 B1 | 8/2005 |
| FR | 2867057 B1 | 6/2007 |
| NL | 7610576 A | 3/1978 |
| WO | WO-9417745 A1 | 8/1994 |
| WO | WO-9519149 A1 | 7/1995 |
| WO | WO-9905980 A1 | 2/1999 |
| WO | WO-2004024011 A1 | 3/2004 |
| WO | WO-2005087121 A1 | 9/2005 |
| WO | WO-2006066685 A1 | 6/2006 |

OTHER PUBLICATIONS

"European Application Serial No. 19161449.4, Extended European Search Report dated Jun. 3, 2019", 5 pgs.

"U.S. Appl. No. 14/705,575, Examiners Interview Summary dated May 10, 2017", 2 pgs.

"U.S. Appl. No. 14/705,575, Final Office Action dated Mar. 29, 2017", 10 pgs.

"U.S. Appl. No. 14/705,575, Non Final Office Action dated Dec. 9, 2016", 7 pgs.

"U.S. Appl. No. 14/705,575, Notice of Allowance dated Oct. 10, 2017", 8 pgs.

"U.S. Appl. No. 14/705,575, Response filed Mar. 3, 2017 to Non Final Office Action dated Dec. 9, 2016", 8 pgs.

"U.S. Appl. No. 14/705,575, Response filed Jun. 7, 2017 to Final Office Action dated Mar. 29, 2017", 13 pgs.

"U.S. Appl. No. 14/705,575, Response filed Oct. 27, 2016 to Restriction Requirement dated Aug. 29, 2016", 10 pgs.

"U.S. Appl. No. 14/705,575, Restriction Requirement dated Aug. 29, 2016", 9 pgs.

"European Application Serial No. 08728790.0, Extended European Search Report dated cc", 6 pgs.

"European Application Serial No. 08728790.0, Response filed Jun. 5, 2013 to Extended European Search Report dated Nov. 7, 2012", 9 pgs.

"European Application Serial No. 15178751.2, Extended European Search Report dated Dec. 16, 2015", 7 pgs.

"European Application Serial No. 17199929.5, Extended European Search Report dated Feb. 2, 2018", 8 pgs.

* cited by examiner

SPINAL STABILIZATION SYSTEM WITH RIGID AND FLEXIBLE ELEMENTS

CROSS-REFERENCE TO RELATED APPLICATIONS

This application is a divisional of U.S. patent application Ser. No. 14/705,575, filed on May 6, 2015, now U.S. Pat. No. 9,888,944, which issued on Feb. 13, 2018, which is a continuation of U.S. patent application Ser. No. 13/241,696, filed on Sep. 23, 2011, now U.S. Pat. No. 9,034,018, which issued on May 19, 2015, which is a continuation of U.S. patent application Ser. No. 11/688,961, filed on Mar. 21, 2007, now U.S. Pat. No. 8,057,516, which issued on Nov. 15, 2011, the entire disclosures of which are incorporated herein by reference.

TECHNICAL FIELD

This invention relates to spinal stabilization systems, and more particularly to such systems including both a rigid element and a flexible element.

BACKGROUND

The spinal column is a highly complex system of bones and connective tissues that provides support for the body and protects the delicate spinal cord. The spinal column includes a series of vertebrae stacked one on top of the other, each vertebral body including an inner or central portion of relatively weak cancellous bone and an outer portion of relatively strong cortical bone. The vertebrae in the cervical, thoracic, and lumbar regions of the spine are separated by intervertebral discs, which serve as cushions between adjacent vertebrae to dampen compressive forces experienced by the spine. A vertebral canal containing the spinal cord is formed by the intervertebral foramen of the vertebrae. In spite of the complexities, the spine is a highly flexible structure, capable of a high degree of curvature and twist in nearly every direction. For example, the kinematics of the spine normally includes flexion, extension, rotation, and lateral bending.

There are many types of conditions that can lead to significant pain and affect movement of the spine, including spinal disorders such as scoliosis (abnormal lateral curvature of the spine), kyphosis (abnormal forward curvature of the spine, usually in the thoracic spine), excess lordosis (abnormal backward curvature of the spine, usually in the lumbar spine), and spondylolisthesis (forward displacement of one vertebra over another, usually in a lumbar or cervical spine), as well as conditions caused by abnormalities, disease, or trauma, such as ruptured or slipped discs, degenerative disc disease, fractured vertebra, and the like. In addition to causing pain, these conditions may also threaten the critical elements of the nervous system housed within the spinal canal.

One of the most common methods for treating these conditions is to immobilize a portion of the spine to allow treatment. Traditionally, immobilization has been accomplished by rigid stabilization. For example, in a conventional spinal fusion procedure, a surgeon restores the alignment of the spine or the disc space between vertebrae by installing a rigid fixation rod between pedicle screws secured to adjacent vertebrae. Bone graft is placed between the vertebrae, and the fixation rod cooperates with the screws to immobilize the two vertebrae relative to each other so that the bone graft may fuse with the vertebrae.

Dynamic stabilization has also been used in spinal treatment procedures. Dynamic stabilization does not result in complete immobilization, but instead permits enhanced mobility of the spine while also providing sufficient stabilization to effect treatment. One example of a dynamic stabilization system is the Dynesys® system available from Zimmer, Inc. of Warsaw, Ind. Such dynamic stabilization systems typically include a flexible spacer positioned between pedicle screws installed in adjacent vertebrae of the spine. Once the spacer is positioned between the pedicle screws, a flexible cord is threaded through a channel in the spacer. The flexible cord is also secured to the pedicle screws by a housing and set screw, thereby retaining the spacer between the pedicle screws while cooperating with the spacer to permit mobility of the spine.

In some instances, it is desirable to immobilize a portion of the spine using a rigid stabilization system without significantly limiting the mobility or increasing the stress on nearby areas of the spine. Although combining the rigid stabilization system with a dynamic stabilization system would help achieve this objective, there are several challenges associated with doing so. Specifically, there are several challenges associated with combining a flexible element, such as a braided polymer cord, with a rigid element, such as a rigid fixation rod, in a single construct. The cord and rod are ideally connected or coupled to each other before or during a surgical procedure. But the stiffness of the flexible element is often designed to decrease after placement into a patient's body and as treatment occurs to provide increased range of motion. Therefore, a spinal stabilization system in which the rigid element remains sufficiently coupled to the flexible element after this "relaxation" is highly desirable.

SUMMARY

This invention provides a system or construct incorporating both a rigid element and flexible element to stabilize a portion of the spine. The system generally includes first and second anchor members, which may be pedicle screw assemblies, configured to be secured to first and second vertebrae within a patient's body. The rigid element is secured to the first anchor member, while the flexible element secured to the second anchor member. Respective end portions of the rigid and flexible elements are coupled to each other in a manner that securely retains their connection, even after the system has been positioned within the patient's body for an extended period of time.

In some embodiments, the end portion of the flexible element is received over the end portion of the rigid element. For example, the flexible element may be a cord constructed from polymer fibers braided over the end portion of the rigid element. To further facilitate retaining the cord on the rigid element, the fibers may be ultrasonically cut and/or ultrasonically welded to an enlarged ball tip of the rigid element. Such an arrangement increases the amount of surface area in contact between the cord and the rigid element and makes it difficult to pull the cord off the rigid element. A compression-fit collar may also be received over the end portion of the cord so that the fibers are gripped between the ball tip of the rigid element and the collar.

In other embodiments, the end portion of the rigid element includes an axial bore that receives the end portion of the flexible element. The axial bore extends at least partially into the rigid element from an end surface and is shaped to retain an end portion of the flexible element therein. For example, the end portion of the flexible element may include an enlarged section having a first diameter and the axial bore may include a restricted or tapered portion having a second diameter less than the first diameter. The enlarged section of the flexible element may be formed by positioning an insert or plug into the end portion of the flexible element. The restricted portion of the axial bore may be incorporated into the shape of the bore at the time of manufacture or may be formed by swaging a portion of the rigid element.

If desired, the end portion of the rigid element with the axial bore may be received in a housing of a vertebral anchor, such as a pedicle screw assembly. One or more openings extend through an outer surface of the rigid element and into the axial bore. A pin is press-fit into the opening by means of a hand press or by tightening a set screw that secures the rigid element within the housing of the pedicle screw assembly. Because the pin extends into the axial bore, it applies a compression force to the end portion of the flexible element received by the bore. This compression force retains the end portion of the flexible element within the bore.

By virtue of the foregoing, a spinal stabilization system that effectively incorporates aspects of both rigid and dynamic stabilization is provided. The different manners of coupling the rigid element to the flexible element are each designed so that the coupling is maintained even after relaxation of the flexible element over time.

BRIEF DESCRIPTION OF THE DRAWINGS

The accompanying drawings, which are incorporated in and constitute a part of this specification, illustrate exemplary embodiments of the invention and, together with a general description of the invention given above, and the detailed description given below, serve to explain the principles of the invention.

DETAILED DESCRIPTION

Figure 1:
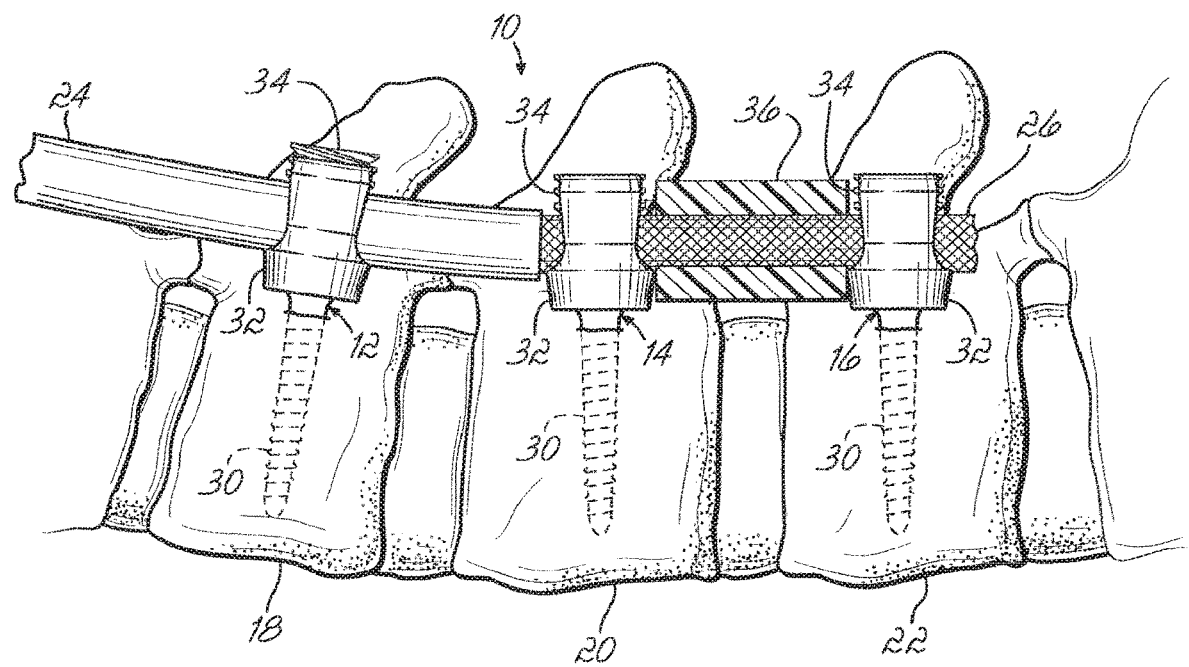
FIG. 1 is a partial side elevational view showing a spinal stabilization system including both a rigid element and a flexible element secured within a patient's body.

FIG. 1 shows one embodiment of a spinal stabilization system or construct 10 according the invention within a patient's body. The stabilization system 10 includes first, second, and third anchor members 12,14,16 secured to respective first, second, and third vertebrae 18, 20, 22 within the patient's body. The anchor members 12,14,16 may be any type of anchor such as a screw or hook designed to cooperate with a rigid element 24 or a flexible element 26 to stabilize a portion of the spine. For example, in the embodiment shown in FIG. 1, the anchor members 12,14,16 are pedicle screw assemblies each having a screw body 30, a housing or retainer 32 coupled to the screw body 30, and a set screw 34. Each housing 32 receives the rigid element 24 or the flexible element 26, which are secured to the associated housing 32 by one of the set screws 34. One example of this type of pedicle screw arrangement is the Optima® Spinal Stabilization System available from Zimmer, Inc. of Warsaw, Ind.

The rigid element 24 and the flexible element 26 each extend between two or more of the pedicle screw assemblies. The rigid element 24 may be a metal rod, such as those commonly used in rigid spinal fixation procedures, while the flexible element 26 may be a cord, such as those commonly used in dynamic stabilization procedures. For example, the flexible element 26 may be constructed from braided polyethylene-terephalate (PET) fibers or other braided polymer fibers. A flexible spacer 36 is received over the flexible element 26 to provide additional support during movement of the spine in some embodiments.

As shown in FIG. 1, the rigid element 24 is coupled to the flexible element 26 between the first and second anchor members 12,14. Such an arrangement enables the overall system or construct 10 to combine the features of both rigid stabilization and dynamic stabilization. In particular, the rigid element 24 enables the system 10 to rigidly immobilize a desired area of the spine to promote fusion or other treatment in a desired area, while the flexible element 26 provides additional stabilization without significantly increasing the stress on nearby vertebrae or compromising mobility. The rigid and flexible elements 24, 26 may be coupled to each other in a variety of different manners, examples of which will be described below with reference to FIGS. 2-11.

Figure 2:
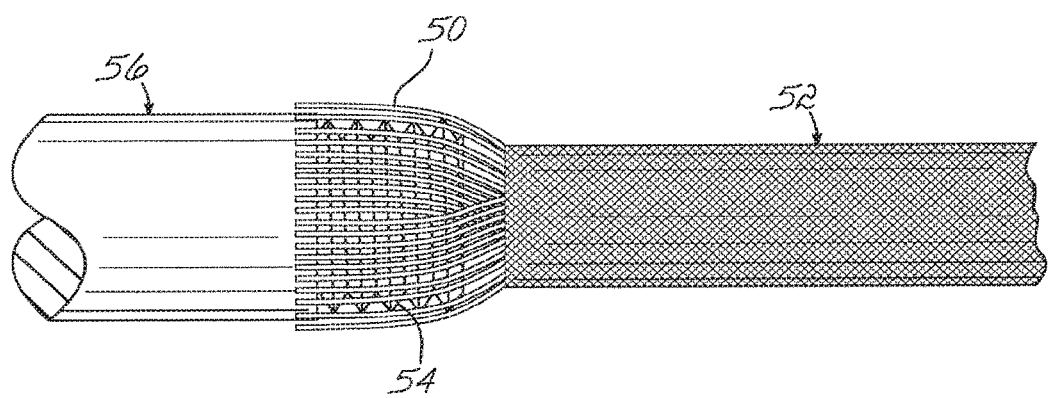
FIG. 2 is a schematic view showing how the rigid and flexible elements of FIG. 1 may be coupled together according to one embodiment of the invention.
Figure 3:
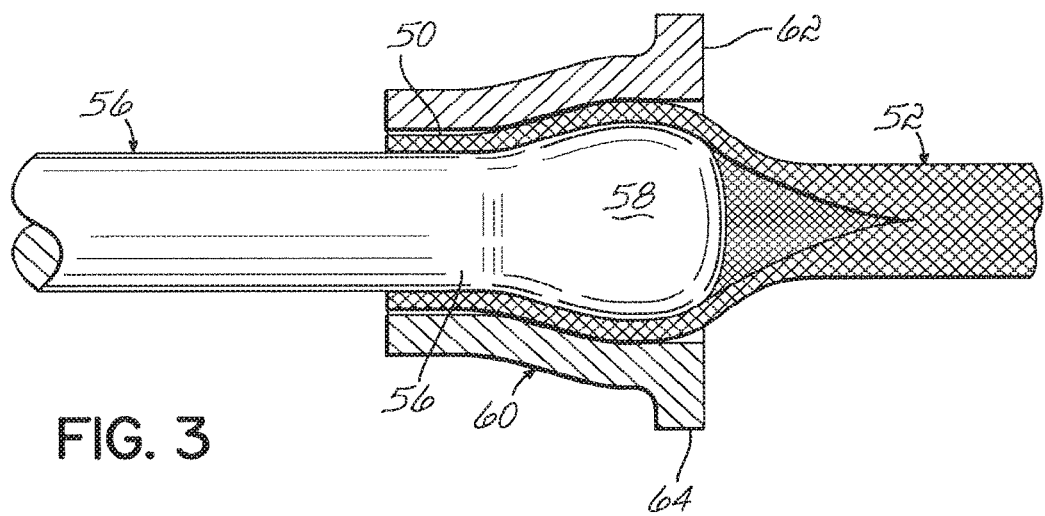
FIG. 3 is a side elevational view, partially in cross-section, showing how the rigid and flexible elements of FIG. 1 may be coupled together according to another embodiment of the invention.

For example, FIGS. 2 and 3 illustrate embodiments in which an end portion 50 of a braided cord 52 is received over an end portion 54 of a rigid fixation rod 56. The end portion 50 of the cord 52 is retained on the end portion 54 of the rod 56, which may be achieved by braiding or weaving the fibers of the cord 52 over the end portion 54. Once this step is complete, the region where the cord 52 overlaps the rod 56 is heat treated in a manner that promotes intimate chemical and physical bonding of the cord 52 to the rod 56. For example, the cord 52 may be ultrasonically welded to the rod 56. Such an arrangement results in the cord 52 being coupled to the rod 56 prior to implantation without placing meaningful stresses on the cord 52 and without the system 10 requiring additional components.

Additionally, as shown in FIG. 3, in some embodiments the end portion 54 of the fixation rod 56 may further include an enlarged ball tip 58. Once the cord 52 is braided over the ball tip 58, the end portion 50 of the cord 52 is cut at location on the rod 56 spaced from the ball tip 58 (i.e., where the cord 52 has a smaller diameter than that of the ball tip) by ultrasonic cutting. The ultrasonic cutting and/or welding results in the fiber ends joining together so that the end portion 50 includes a permanent diameter smaller than the ball tip 58, thereby preventing the cord 52 from fraying and further retaining it on the end portion 54 of the fixation rod 56. The relatively large amount of contact area between the cord 52 and the rod 56 helps distribute any pre or postoperative loads on the cord 52, which in turn minimizes the effects of changes in those loads resulting from post-operative relaxation of the cord 52 or other conditions.

If desired, a collar 60 may also be compression-fitted around the end portion 50 of the cord 52 to further retain the cord 52 on the fixation rod 56. When tension is applied to the cord 52, the collar 60 cooperates with the ball tip 58 to provide a gripping force. The collar 60 includes a polished end surface 62 configured to confront the spacer 36 (FIG. 1), with the end surface 62 optionally defined by a radially extending flange 64. Those skilled in the art will appreciate that the collar 60 may also be designed to interact with one of the pedicle screw assemblies.

Figure 4:
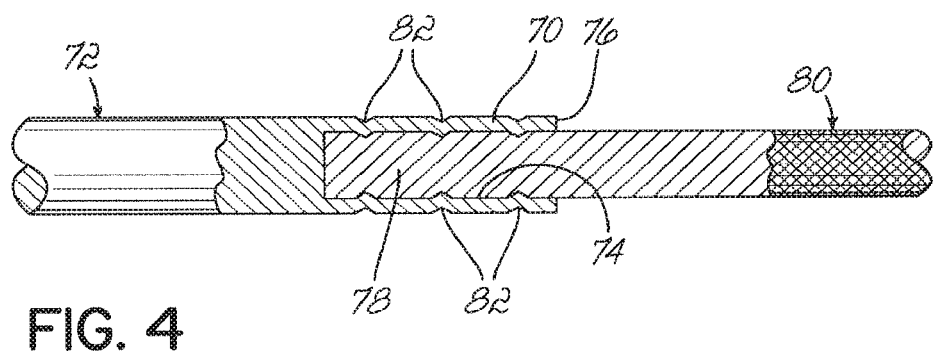
FIG. 4 is a side elevational view, partially in cross-section, showing how the rigid and flexible elements of FIG. 1 may be coupled together according to another embodiment of the invention.

Rather than being received over the end portion of the rigid element 24, the flexible element 26 may be received and retained within a portion of the rigid element 24. For example, FIG. 4 illustrates an embodiment in which an end portion 70 of a fixation rod 72 includes an axial bore 74 extending from an end surface 76. An end portion 78 of a flexible cord 80 is received in the axial bore 74. To retain the cord 80 in the bore 74, the end portion 70 of the fixation rod 72 is swaged (i.e., cold-worked) about its circumference at one or more locations designated by 82. The 360 degree swages 82 place the cord 80 into high, radially-symmetric compression so that it cannot be easily pulled out of the axial bore 74. The swages 82 also provide the end portion 70 of the fixation rod 72 with a rib-like appearance.

Figure 5:
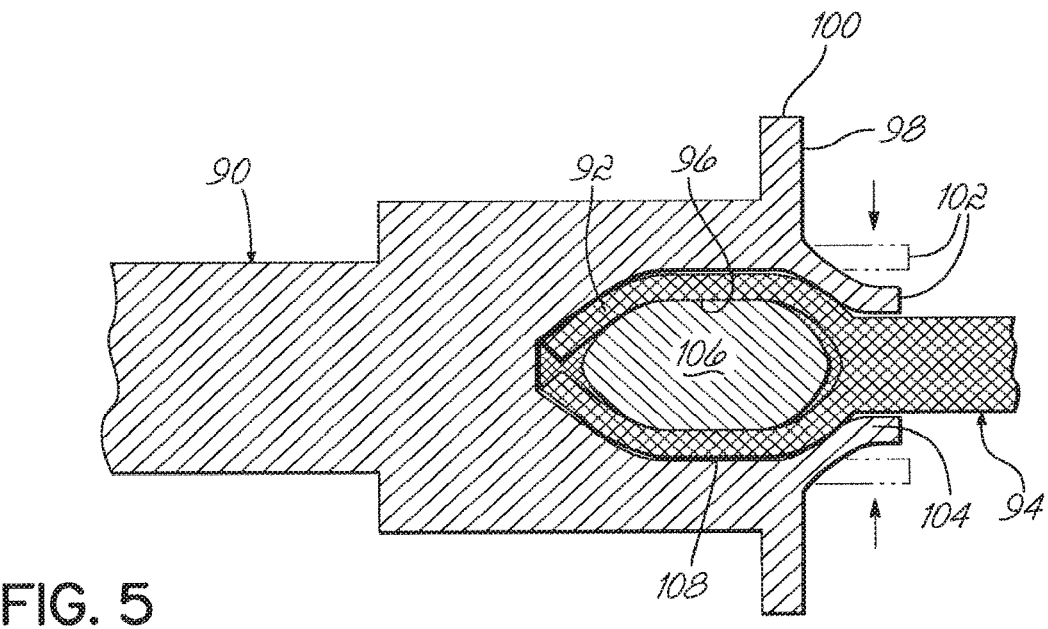
FIG. 5 is cross-sectional view showing how the rigid and flexible elements of FIG. 1 may be coupled together according to another embodiment of the invention.

FIG. 5 also illustrates an embodiment of the spinal stabilization system 10 in which a fixation rod 90 is swaged to retain an end portion 92 of a flexible cord 94 within an axial bore 96. Specifically, the fixation rod 90 terminates in an end surface 98 defined by a radially extending flange 100. The end surface 98 may be configured to confront a spacer 36 (FIG. 1) and further includes flange 102 extending distally therefrom around the opening of the axial bore 96. After the end portion 92 of the cord 94 is inserted into the axial bore 96, the distal flange 102 is swaged in a radially inward direction to define a restricted portion 104 of the axial bore 96. The restricted portion 104 has a diameter less than that of the end portion 92 of the cord 94 so that the cord 94 is retained in the axial bore 96.

For this purpose, the end portion 92 of the cord 94 may include an insert or plug 106 to define an enlarged diameter section 108. The insert 106 may be constructed from metal or any other biocompatible material and is surrounded and retained by the end portion 92 of the cord 94. For example, after weaving fibers of the cord 94 around the insert 106 or positioning the insert 106 in a predefined space within the end portion 92, the cord 94 may be ultrasonically heated while being compressed around the insert 106 in a mold (not shown). This ultrasonic forming process promotes bonding of the cord fibers to the insert 106 and provides the cord 94 with a shape that retains the insert 106 in the end portion 92. Thus, when the end portion 92 of the cord 94 is received in the axial bore 96 and the distal flange 102 is swaged inwardly to define the restricted portion 104, pulling on the cord 94 results in the cord fibers being "wedged" between the insert 106 and the restricted portion 104. This resistance to pull-out remains effective even after warming and relaxation of the cord 94 within a patient's body.

Figure 6:
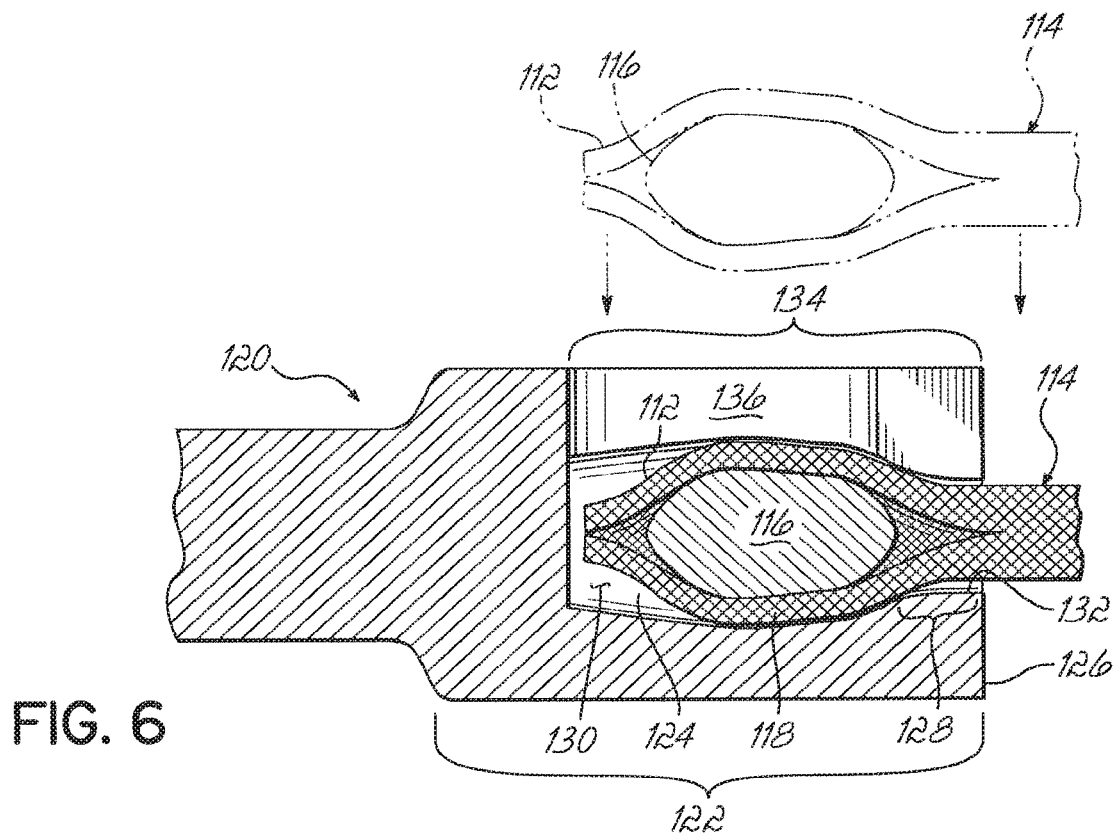
FIG. 6 is a cross-sectional view showing how the rigid and flexible elements of FIG. 1 may be coupled together according to another embodiment of the invention.
Figure 6A:
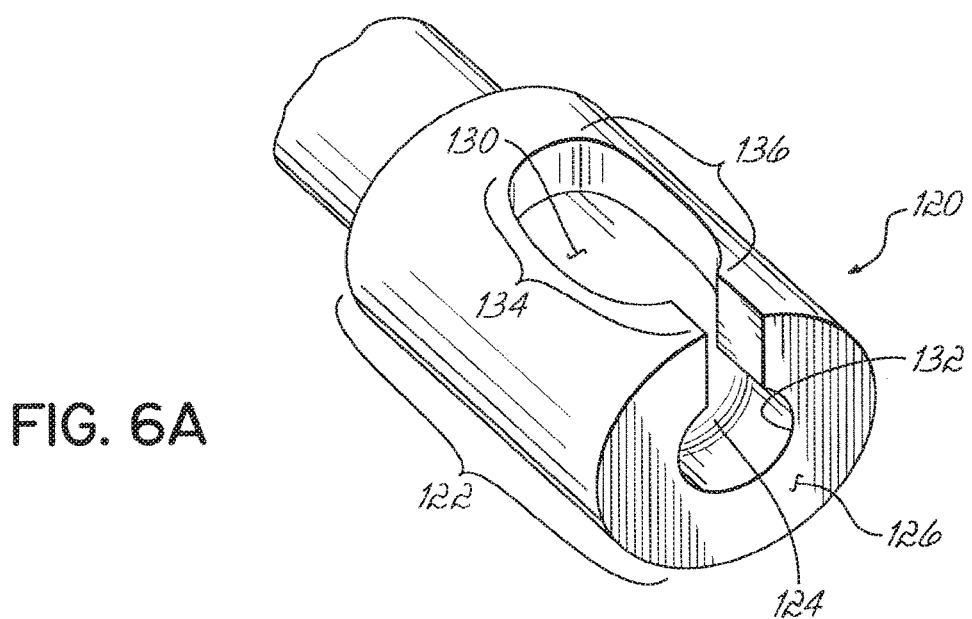
FIG. 6A is a perspective view of a portion of the rigid element shown in FIG. 6.

An embodiment that operates upon similar principles is shown in FIGS. 6 and 6A. In this embodiment, an end portion 112 of a flexible cord 114 is provided with an insert 116 in the same manner as the previous embodiment to define an enlarged diameter section 118. A fixation rod 120 having an enlarged end portion 122 includes an axial bore 124 extending from an end surface 126. The axial bore 124 receives the end portion 112 of the cord 114, but includes a restricted portion 128 having a smaller diameter than that of the enlarged section 118. If desired, an interior surface 130 of the axial bore 124 may be tapered to help define the restricted portion 128 and to define a shape that more closely resembles that of the cord end portion 112.

In this arrangement, the cord 114 cannot be end-loaded into the axial bore 124 through an opening 132 on the end surface 126 of the fixation rod 120. Instead, the end portion 112 of the cord 114 is inserted through a slot 134 on the end portion 122 of the rod 120. The slot 134 extends into the axial bore 124 and includes an enlarged opening 136 to accommodate the enlarged section 118 of the cord 114, as shown in FIG. 6A. Applying tension to the cord 114 after the end portion 112 is received in the axial bore 124 creates a wedge-like effect due to the interference between insert 116 and the restricted portion 128. In other words, as with the embodiment shown in FIG. 5, the fibers of the cord 114 are "wedged" between the insert 116 and the restricted portion 128 to retain the cord 114 within the axial bore 124. The more tension that is placed on the cord 114, the stronger it is gripped between the insert 116 and the restricted portion 128.

The cord 114 may be inserted through the slot 134 and into the axial bore 124 prior to or even during an operation because of the pre-formed shape of the fixation rod 120. For example, during a surgical procedure, the rod 120 may first be secured to a top-loading pedicle screw 30 (FIG. 1) using the housing 32 and set screw 34. After inserting the end portion 112 of the cord 114 through the slot 134 and into the axial bore 124, the cord 114 may then be secured to a different pedicle screw assembly to stabilize the entire construct 10. Because the cord 114 is not put under any stress prior to insertion into the patient's body, concerns about stress relaxation during storage are avoided. Additionally, if further surgical procedures are later required to effect treatment, the cord 114 may be easily replaced without requiring removal of the fixation rod 120. This is particularly advantageous when seeking to modify the amount of dynamic stabilization provided by the entire construct 10 by replacing the original cord 114 with a different one.

Figure 7:
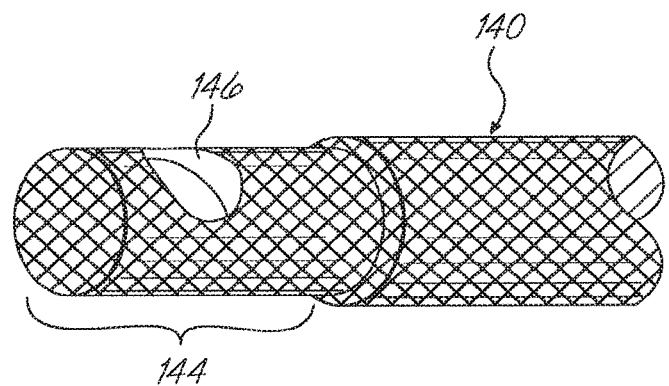
FIG. 7 is a perspective view showing a portion of the flexible element of FIG. 1 according to another embodiment of the invention.
Figure 8:
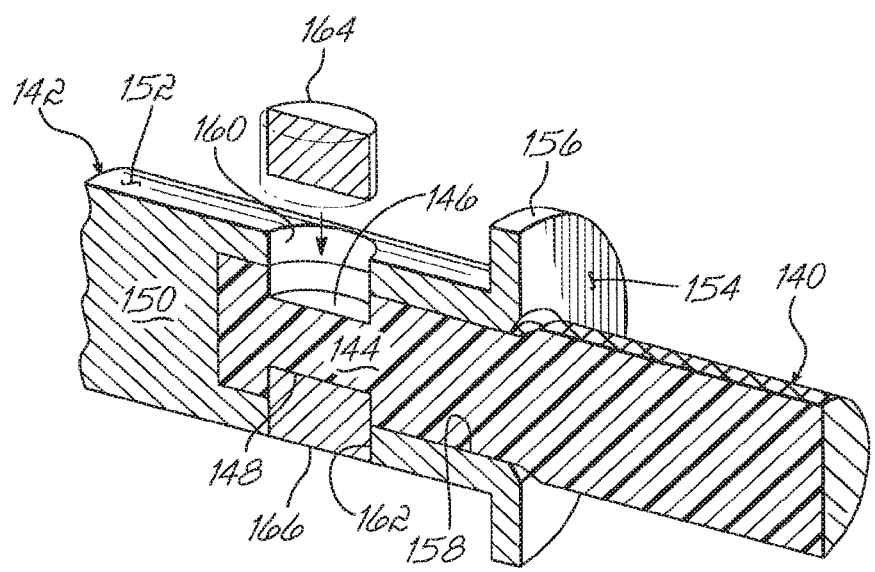
FIG. 8 is a cross-sectional perspective view showing how the flexible element of FIG. 6 may be coupled to the rigid element of FIG. 1.

FIGS. 7 and 8 illustrate another embodiment in which a cord 140 may be coupled to a rigid element 142 between the first and second anchor members 12,14 (FIG. 1). In this embodiment, the cord 140 is provided with a preformed shape. For example, the cord 140 may be constructed from polymer fibers and may be ultrasonically heated while being compressed in a mold. This ultrasonic forming process in one embodiment results in an end portion 144 of the cord 140 having a reduced diameter and first and second recesses 146,148.

The rigid element 142 includes an end portion 150 with an outer surface 152 and an end surface 154. The end surface 154 is defined by a radially extending flange 156 and configured to confront the spacer 36 (FIG. 1). An axial bore 158 extends into the end portion 150 from the end surface 154, and the outer surface 152 includes first and second openings or holes 160,162 extending into the axial bore 158. The axial bore 158 receives the end portion 144 of the cord 140, with the first and second openings 160,162 aligned with the respective first and second recesses 146,148. To retain the cord 140 within the axial bore 158, first and second fasteners 164,166 are inserted through the respective first and second openings 160,162 until they are received in the respective first and second recesses 146,148. Because the first and second recesses 146,148 are permanently formed in the end portion 144 of the cord 140, relaxation of the cord 140 has minimal or no affect on the engagement between the first and second recesses 146,148 and the first and second fasteners 164,166.

The fasteners 164,166 shown in FIG. 8 are pins that are press-fit into the first and second openings 160,162. It will be appreciated, however, that a wide variety of other types of fasteners (screws, rings, clips, etc.) may be secured within the first and/or second openings 160,162 to retain the end portion 144 of the cord 140 within the axial bore 158. It will also be appreciated that only one fastener may be used to retain the cord 140 and that the axial bore 158 of the rigid element 142 maybe shaped with features adapted to cooperate with the preformed shaped of the cord 140. For example, rather than including the second opening 162, the rigid element 142 may be machined to define a protrusion (not shown) in the axial bore 158 at the same location. The protrusion would cooperate with the second recess 148 to retain the end portion 144 of the cord 140 in the axial bore 158. The end portion 144 of the cord 140 and axial bore 158 of the rigid element 142 may therefore be shaped in a variety of different manners to achieve this type of relationship.

Figure 9:
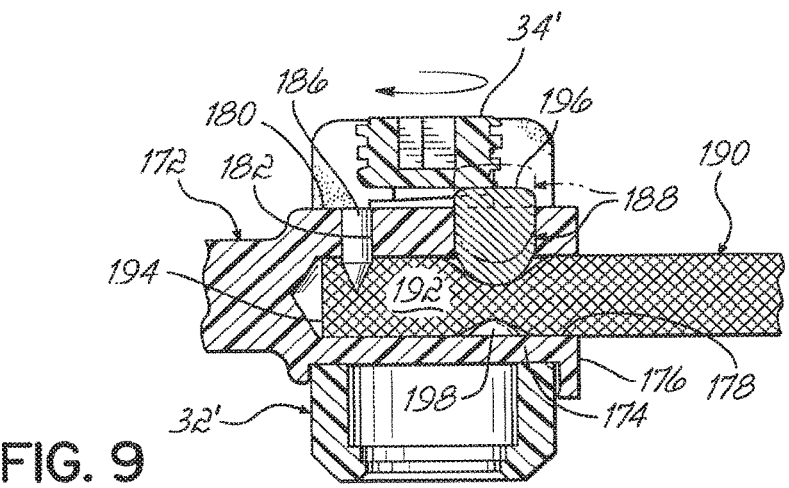
FIG. 9 is a cross-sectional side view showing the rigid and flexible elements of FIG. 1 according to another embodiment of the invention.
Figure 10:
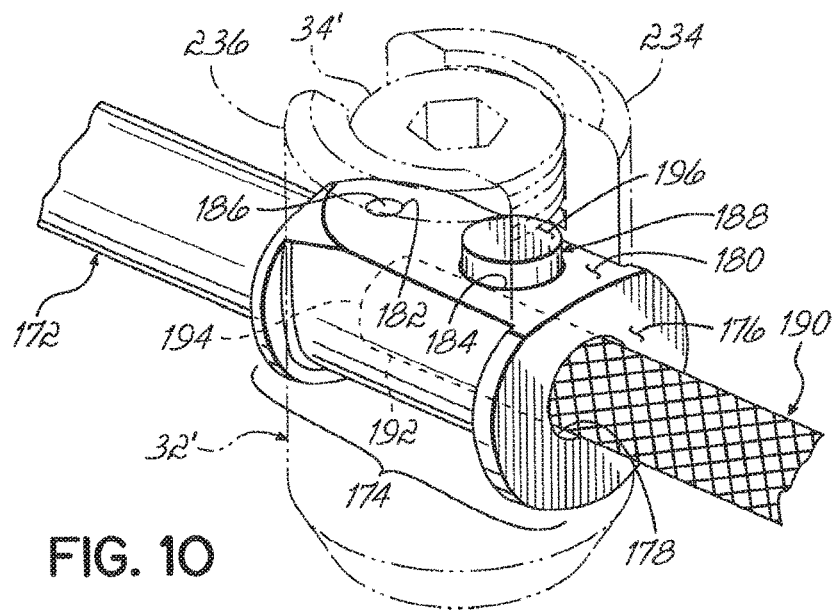
FIG. 10 is a perspective view showing how the rigid and flexible elements of FIG. 9 may be coupled together.
Figure 11:
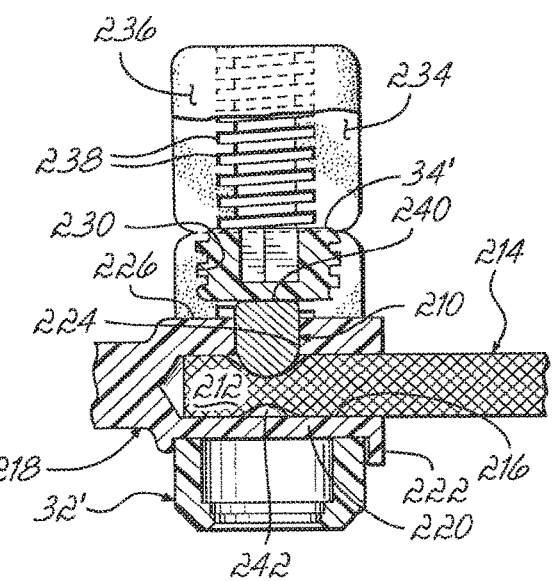
FIG. 11 is a partial side elevational view, partially in cross-section, showing how the rigid and flexible elements of FIG. 1 may be coupled together according to another embodiment of the invention.

FIGS. 9-11 illustrate embodiments of the system 10 shown in FIG. 1 in which the rigid member 24 is shaped to cooperate with one of the pedicle screw assemblies 12,14,16 to retain the flexible element 26 within a portion thereof. The housings 32 and set screws 34 shown in FIG. 1 have a different configuration in the embodiments shown in FIGS. 9-11 and will be indicated with prime marks (') in the description below.

To this end, FIGS. 9 and 10 illustrate a rigid element 172 having an end portion 174 received in the housing 32' of a pedicle screw assembly. The end portion 174 includes an end surface 176 configured to confront a spacer 36 (FIG. 1), an axial bore 178 extending from the end surface 176, an outer surface 180, and first and second openings 182,184 on the outer surface 180 extending into the axial bore 178. The first opening 182 has a relatively small diameter and receives a needle member 186, while the second opening 184 has a larger diameter and receives a pin 188. An interference fit may be provided between the needle member 186 and the first opening 182 and the pin 188 and the second opening 184.

A flexible element 190, such as a cord constructed from braided polymer fibers, includes an end portion 192 received in the axial bore 178. The flexible element 190 is initially secured within the axial bore 178 by inserting the needle member 186 through the first opening 182. The manufacturer typically accomplishes this step so that the construct is pre-assembled with the flexible element 190 coupled to the rigid element 172 prior to delivery to the customer. The needle member 186 engages the cord 190 proximate an end 194, which serves little function in terms of ultimately providing stabilization once in a patient's body.

The pin 188 may also be partially inserted into the second opening 184 by the manufacturer, but is not advanced far enough to place any appreciable stresses on the cord 190. Instead, the final pressing of the pin 188 is accomplished prior to use with a hand press (not shown) or other similar tool. The pin 188 is ideally advanced through the second opening 184 until a top surface 196 of the pin 188 becomes substantially flush with the outer surface 180 of the rigid element 172. Such an arrangement prevents the pin 188 from interfering with the operation of the set screw 34', which secures the rigid element 172 to the housing 32' of the pedicle screw assembly.

The pin 188 compresses the flexible element 190 within the axial bore 178 to retain the flexible element 190 therein. A protrusion 198, such as a bump or rib, may be provided in the axial bore 178 opposite the second opening 184 so that the flexible element 190 is gripped between the pin 188 and the protrusion 198. The pin 188 applies sufficient force to securely retain the cord 190 even after relaxation once inserted into a patient's body. Although only a press-fit pin is shown, any type of fastener capable of applying forces to the cord 190 may be used instead.

FIG. 11 shows a similar embodiment having a pin 210 for retaining an end portion 212 of a flexible element 214 within an axial bore 216 of a rigid element 218. As with the previous embodiment, the axial bore 216 is positioned within an end portion 220 of the rigid element 218 received in the housing 32' of a pedicle screw assembly and has an end surface 222 configured to confront the spacer 36 (FIG. 1). An opening 224 on an outer surface 226 of the end portion 220 extends into the axial bore 216 and is aligned with the set screw 34' received in the housing 32'. The set screw 34' normally engages internal threads 230 to secure the end portion 220 of the rigid element in a socket defined by the housing 32'. To accommodate for the pin 210, the housing 32' further includes first and second tabs 234, 236 extending upwardly. Each of the first and second tabs 234, 236 includes internal threads 238 as well.

In use, the end portion 212 of the flexible element 214 is inserted into the axial bore 216. The pin 210 is then inserted into the opening 224 and the set screw 34' is advanced along the internal threads 238 of the first and second tabs 234, 236 until it contacts a top surface 240 of the pin 210. To secure the flexible element 214 within the axial bore 216, the set screw 34' is further advanced to engage the internal threads 230 of the housing 32' and to push the pin 210 into the opening 224. The set screw 34' is advanced until the top surface 240 of the pin 210 is substantially flush with the outer surface 226 of the rigid element 218. In this position, the pin 210 applies a sufficient compression force to retain the end portion 212 of the flexible element 214 within the axial bore. One or more protrusions 242 or the like may be provided within the axial bore 216 to help grip the flexible element 214, much like the previous embodiment.

Thus, the flexible element 214 may be secured to the rigid element 218 without any additional tools. The same tool normally used to secure the set screw 34' is used to advance the pin 210 into the axial bore 216. Although the pin 210 and set screw 34' are shown as separate components, they may alternatively be integrally formed as a single component. The first and second tabs 234, 236 may also be configured to be removed from the housing 32' after the set screw 34' is completely advanced. In particular, the first and second tabs 234, 236 serve to distribute the force applied to the housing 32' while tightening the set screw 34' with a screwdriver or other tool. The tabs 234, 236 may be frangibly connected or otherwise separable from the housing 32' of the pedicle screw assembly. Once the set screw 34' is advanced so that it only engages the internal threads 230 of the housing 32', the first and second tabs 234, 236 may be broken off from the housing 32' and removed.

While the invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. For example, although the rigid element is primarily described above as a metal rod, those skilled in the art will appreciate that "rigid" is a relative term. To this end, the rigid element may be a metal cable and the flexible element may be a polymer cord. The cable and cord may be coupled using the techniques described above or may simply be spliced together.

Therefore, the invention in its broader aspects is not limited to the specific details, representative apparatus and methods, and illustrative examples shown and described. Accordingly, departures may be made from such details without departing from the scope or spirit of the general inventive concept.

What is claimed:

1. A method of securing a flexible ent in a spinal stabilization system, comprising:
   securing an anchor member to a vertebra of a patient, the anchor member including a threaded shank and a housing having internal threads attached to the threaded shank;
   inserting a rigid element into the housing of the anchor member, the rigid element having a flexible element extending into an axial bore extending into the rigid element and a fastener extending into an opening on an outer surface of the rigid element which intersects the axial bore;
   rotatably engaging a set screw with the internal threads of the housing to advance the fastener in the opening of the rigid element into engagement with the flexible element; and
   securing the rigid element within the housing with the set screw.

2. The method of claim 1, wherein the fastener is a separate component from the set screw.

3. The method of claim 2, wherein the fastener is aligned with the set screw and rotatably engaging the set screw with the internal threads of the housing brings the set screw into contact with the fastener prior to advancing the fastener into engagement with the flexible element in the axial bore.

4. The method of claim 1, wherein the fastener is integrally formed with the set screw as a single component.

5. The method of claim 1, wherein advancing the fastener into engagement with the flexible element compresses the flexile element within the axial bore.

6. The method of claim 1, further including removing first and second tabs from the housing.

7. The method of claim 1, wherein the rigid element includes a protrusion extending into the axial bore.

8. The method of claim 7, wherein the protrusion extends into the axial bore opposite the opening.

9. The method of claim 7, wherein advancing the fastener into engagement with the flexible element compresses the flexible element between the protrusion and the fastener.

10. The method of claim 1, wherein the axial bore extends into the rigid element from an end surface of the rigid element.

11. The method of claim 1, wherein the rigid element is inserted into the housing of the anchor member in a direction transverse to the axial bore.

12. A method of assembling a spinal stabilization system having a flexible element, the method comprising:
   assembling an anchor member by inserting a threaded shank into a housing having internal threads;
   inserting a rigid element into the housing of the anchor member, the rigid element comprising:
      an axial bore extending into a first axial end of the rigid element;
      a flexible element extending from the axial bore; and
      a rod element extending from a second axial end of the rigid element;
   radially sliding a fastener into the rigid element to engage the flexible element and secure the flexible element to the rigid element; and
   inserting a closure member into the housing to secure the rigid element to the housing;
   wherein the fastener comprises a pin and the closure member is configured to push the fastener into the flexible element.

13. The method of claim 12, further comprising:
   inserting the flexible element into the axial bore; and
   positioning a needle element in the axial bore to engage the flexible element.

14. The method of claim 12, further comprising force fitting the fastener into the rigid element.

15. The method of claim 12, further comprising:
   positioning the rod element into a housing of a first adjacent anchor member; and
   positioning the flexible element into a housing of a second adjacent anchor member.

16. A method of securing a flexible element in a spinal stabilization system, comprising:
   securing a first anchor member to a first vertebra of a patient, the first anchor member including a first threaded shank and a first housing having internal threads attached to the first threaded shank;
   inserting a rod element into the first housing of the first anchor member, the rod element including a flexible element extending from an axial end thereof;
   securing a second anchor member to a second vertebra of the patient, the second anchor member including a second threaded shank and a second housing having internal threads attached to the second threaded shank;
   inserting the flexible element into the second housing of the second anchor member;
   securing the rod element to the first housing and the flexible element to the rod element using a first closure member; and
   additionally securing the flexible element to the rod element with a needle member.

17. The method of claim 16; further comprising:
   engaging external threads of the first closure member with the internal threads of the first housing to secure the rod element to the first housing; and
   pushing a pin element into the flexible element with the first closure member to secure the flexible element to the rod element.

18. The method of claim 16, further comprising engaging external threads of a second closure member with the internal threads of the second housing to secure the flexible element to the second housing.

19. The method of claim 16, further comprising positioning a spacer along the flexible element adjacent the second housing.

\* \* \* \* \*

UNITED STATES PATENT AND TRADEMARK OFFICE
CERTIFICATE OF CORRECTION

PATENT NO. : 10,631,898 B2  
APPLICATION NO. : 15/861320  
DATED : April 28, 2020  
INVENTOR(S) : Zylber et al.

Page 1 of 1

It is certified that error appears in the above-identified patent and that said Letters Patent is hereby corrected as shown below:

On the Title Page

Item (72), in "Inventors", in Column 1, Line 1, delete "Marseilles" and insert --Marseille-- therefor Item (60), under "Related U.S. Application Data", Line 1, delete "(60)" and insert --(62)-- therefor In the Claims In Column 9, Line 26, in Claim 1, delete "ent" and insert --element-- therefor In Column 10, Line 54, in Claim 17, delete "16;" and insert --16,-- therefor Signed and Sealed this  
Twenty-eighth Day of July, 2020

Andrei Iancu  
*Director of the United States Patent and Trademark Office*